(12) United States Patent
Zhao (10) Patent No.: US 12,090,108 B2
(45) Date of Patent: Sep. 17, 2024

(54) MASSAGE ROLLER AND CONDUCTIVE STRUCTURE THEREOF

(71) Applicant: Xiamen High Top Electronic Technology Co., Ltd., Xiamen (CN)

(72) Inventor: Liangsan Zhao, Xiamen (CN)

(73) Assignee: Xiamen High Top Electronic Technology Co., Ltd., Xiamen (CN)

( * ) Notice: Subject to any disclaimer, the term of this patent is extended or adjusted under 35 U.S.C. 154(b) by 1037 days.

(21) Appl. No.: 17/023,320

(22) Filed: Sep. 16, 2020

(65) Prior Publication Data

US 2022/0031561 A1 Feb. 3, 2022

(30) Foreign Application Priority Data

Jul. 30, 2020 (CN) .......................... 202010750320.4

(51) Int. Cl.
| | |
|---|---|
| A61H 15/00 | (2006.01) |
| A61H 15/02 | (2006.01) |
| A61N 5/06 | (2006.01) |
| H05K 1/02 | (2006.01) |

(52) U.S. Cl.
CPC ......... *A61H 15/02* (2013.01); *A61H 15/0078* (2013.01); *A61N 5/06* (2013.01); *H05K 1/0296* (2013.01); *A61H 2201/10* (2013.01); *A61H 2201/1671* (2013.01); *A61N 2005/0659* (2013.01); *H05K 2201/10234* (2013.01)

(58) Field of Classification Search
CPC ..................................................... A61H 15/02
See application file for complete search history.

(56) References Cited

U.S. PATENT DOCUMENTS

| | | | | |
|---|---|---|---|---|
| 3,358,278 | A | * 12/1967 | Jackson | H03M 1/00 341/13 |
| 3,850,035 | A | * 11/1974 | Seabury, Jr. | G01L 5/103 73/862.08 |
| 8,556,835 | B2 | * 10/2013 | Ferber | A61H 7/004 601/84 |
| 2019/0246780 | A1 | * 8/2019 | Jungnickel | A61C 17/222 |

* cited by examiner

*Primary Examiner* — LaToya M Louis
(74) *Attorney, Agent, or Firm* — Bayramoglu Law Offices LLC (57) ABSTRACT

A conductive structure of a massage roller includes a working circuit board, a conductive base, a conductive plate, two first conductive parts and two second conductive parts. The working circuit board and the conductive plate are positioned at upper and lower ends of the conductive base respectively. The conductive base is provided with at least a pair of accommodating cavities, and conductors are placed in the accommodating cavities. The two first conductive parts are positioned on the bottom surface of the working circuit board, and the first conductive parts are connected with the working circuit board. The two second conductive parts are positioned on the top surface of the conductive plate, and the second conductive parts are connected with the conductive plate; and the top surfaces of the conductors abut against the two first conductive parts, and the bottom surfaces of the conductors abut against the two second conductive parts.

9 Claims, 8 Drawing Sheets

MASSAGE ROLLER AND CONDUCTIVE STRUCTURE THEREOF

CROSS REFERENCE TO THE RELATED APPLICATIONS

This application is based upon and claims priority to Chinese Patent Application No. 202010750320.4, filed on Jul. 30, 2020, the entire contents of which are incorporated herein by reference.

TECHNICAL FIELD

The disclosure relates to the technical field of massagers, in particular to a massage roller and a conductive structure thereof.

BACKGROUND

With the continuous improvement of living standards, health care products have become more and more popular. Massagers are common physical therapy instruments for health care, which can promote local blood circulation and accelerate metabolism of the human body, making people feel more relaxed and less fatigued at the end of a day.

The most important components of the massagers are massage rollers and conductive structures thereof. In order to achieve a better massage effect, a light panel is often arranged at a massage head of an existing massage roller, and the light irradiated by light beads of the light panel can promote the blood circulation of a user, thereby enhancing the massage effect of the massager. However, it is not easy to install a circuit board at the rotating massage head and make the circuit board connected with electronic control elements inside the massage roller while ensuring the service life of the massager. The currently adopted method is as follows: a conductive brush is installed in the circuit board inside the massage head as a conductive structure, and electric conduction is realized through the frictional contact between the rotating conductive brush and a stationary conductive ring on a conductive plate. According to this technology, electric conduction is realized by means of the conductive brush, and hard friction can be generated due to prolonged contact between the conductive contact surfaces of the conductive brush and the conductive ring, which will cause certain loss to a conductor; and once the conductive brush is overused, it can no longer make contact with the conductive ring to conduct electricity, and the circuit board in the massage head will have the problem of poor contact or open circuit, which will affect user experience and shorten the service life of the massager.

SUMMARY

The purpose of the disclosure is to provide a massage roller and a conductive structure thereof. The conductive structure can not only keep the electrical connection between a working circuit board in a massage head and the massage roller, but also effectively reduce the loss at a conductive part, thus avoiding the formation of an open circuit after a long-term use of the circuit board, and prolonging the service life of a massager.

In order to achieve the above purpose, the solution of the disclosure is as follows: a conductive structure of a massage roller includes a working circuit board, a conductive base, a conductive plate, two first conductive parts and two second conductive parts, wherein the working circuit board and the conductive plate are positioned at upper and lower ends of the conductive base respectively; the conductive base is provided with at least one pair of accommodating cavities, and conductors are placed in the at least one pair of accommodating cavities; the two first conductive parts are positioned on a bottom surface of the working circuit board, and both of the two first conductive parts are connected with the working circuit board; the two second conductive parts are positioned on a top surface of the conductive plate, and both of the two second conductive parts are connected with the conductive plate; and top surfaces of the conductors are connected with the two first conductive parts in an abutting mode respectively, and bottom surfaces of the conductors are connected with the two second conductive parts in an abutting mode respectively.

Further, the working circuit board is an infrared light panel.

Further, the two first conductive parts are positioned above the two second conductive parts, the two first conductive parts are concentric circles, the two second conductive parts and the two first conductive parts have a same shape and size, and the at least one pair of accommodating cavities corresponds to the two first conductive parts and the two second conductive parts.

Further, the conductors are conductive steel balls, and diameters of the conductors are less than or equal to diameters of the at least one pair of accommodating cavities.

A massage roller, comprising a massage head, an upper roller cover, a center box cover, a lower roller cover, a control circuit board and a driving mechanism; the massage head is rotatably connected to a top surface of the upper roller cover; the upper roller cover is detachably connected above the lower roller cover; the center box cover is positioned on a top surface of one side of the upper roller cover; the control circuit board is positioned at one side of the center box cover; the driving mechanism is fixed between a locking upper roller cover and the lower roller cover and used for driving the massage head to rotate; and further comprises the conductive structure mentioned above; the working circuit board of the conductive structure is fixed inside the massage head, and the conductive base and the conductive plate are fixed on the upper roller cover below the massage head.

Further, the massage head includes an upper massage head cover and a lower massage head cover; the upper massage head cover is detachably connected above the lower massage head cover; a center of the lower massage head cover is provided with a cavity, and the working circuit board is detachably and can be connected above the cavity of the lower massage head cover; and the conductive base and the conductive plate are positioned in the cavity of the lower massage head cover.

Further, a cushion block is arranged between a bottom of the massage head and the upper roller cover, and the conductive base and the conductive plate are placed above the cushion block.

Further, the lower roller cover comprises a housing, a main fixed leg, an auxiliary fixed leg, an accommodating groove and a connecting fixed leg; the accommodating groove is formed in a center of an interior of the housing, and the main fixed leg, the auxiliary fixed leg and the connecting fixed leg are positioned inside the housing outside the accommodating groove; and the auxiliary fixed leg and the connecting fixed leg are positioned at two ends of the main fixed leg respectively.

Further, the driving mechanism at least includes a main gear, an auxiliary gear, a driving gear, a motor, a main linkage gear, an auxiliary linkage gear and a traveling gear; the main gear and the auxiliary linkage gear are installed on the main fixed leg in a sleeving mode respectively, and the main gear is positioned above the auxiliary linkage gear; the auxiliary gear and the driving gear are installed on the auxiliary fixed leg in a sleeving mode respectively, the auxiliary gear is positioned above the driving gear, and the auxiliary gear meshes with the main gear mutually; the motor is positioned in the accommodating groove, and an output end of the motor is connected with a screw rod, wherein the screw rod meshes with the driving gear mutually; and the main linkage gear and the traveling gear are installed on the connecting fixed leg in a sleeving mode respectively, the main linkage gear is positioned above the traveling gear, and the main linkage gear meshes with the auxiliary linkage gear mutually.

Further, a center of the main gear is provided with a columnar protrusion, wherein the columnar protrusion penetrates through the conductive structure and is connected with the massage head.

Compared with the prior art, the disclosure has the beneficial effects that:
1. By adopting the conductive structure, the working circuit board and the conductive plate are placed on two sides of the conductive base and are in contact with the conductors; during the rotation of the working circuit board along with the massage head, the pair of first conductive parts of the working circuit board and the pair of second conductive parts of the conductive plate are in contact with the conductors all the time, thus keeping the working circuit board in an electrified state; besides, the rotating conductors can effectively avoid local hard friction of a conductive contact surface, thus reducing friction loss of the conductors and avoiding poor contact and open circuit of the working circuit board; therefore, not only the conductive effect is good, but also the service life of the entire massage roller is greatly prolonged.
2. By adopting the massage roller, the working circuit board arranged inside the massage roller can also be electrified to work during the rotation of the massage head of the massage roller, so that the light beads on the working circuit board can irradiate the skin tissue of the user, promoting the blood circulation of the user and improving the massage effect of the massage head; besides, the auxiliary linkage gear of the driving mechanism rotates synchronously with the main gear, and engages with the main linkage gear to rotate, and the traveling gear can rotate synchronously with the main linkage gear, so that the massage roller moves along a guide rail in a massager housing under the action of a rack, and then an all-around massage can be provided to the user by the moving massage roller and the rotating massage head.

DESCRIPTION OF REFERENCE NUMERALS massager housing 1;
machine body 11;
guide rail 12;
rack 13;
massage roller 2;
massage head 21, upper massage head cover 211, lower massage head cover 212;
upper roller cover 22;
center box cover 23;
lower roller cover 24, housing 241, main fixed leg 242, auxiliary fixed leg 243, connecting fixed leg 244;
control circuit board 25;
conductive structure 26, working circuit board 261, conductor 262, conductive base 263, accommodating cavity 263', conductive plate 264, cushion block 265, first conductive part 266, first conductive ring 2661, second conductive ring 2662, second conductive part 267, third conductive ring 2671, fourth conductive ring 2672;
driving mechanism 27, main gear 271, auxiliary gear 272, driving gear 273, motor 274, screw rod 275, main linkage gear 276, auxiliary linkage gear 277, traveling gear 278; and massager 100.

DETAILED DESCRIPTION OF THE EMBODIMENTS

Embodiments of the disclosure are described in detail below, examples of which are shown in the accompanying drawings, in which identical or similar reference numerals denote identical or similar elements or elements having identical or similar functions throughout. The embodiments described below by referring to the drawings are exemplary and are intended to explain the disclosure, but cannot be understood as limiting the disclosure.

Embodiment 1

As shown in FIGS. 1-3 and 8, a conductive structure 26 of a massage roller includes a working circuit board 261, a conductive base 263, a conductive plate 264, two first conductive parts 266 and two second conductive parts 267, and the working circuit board 261 and the conductive plate 264 are positioned at upper and lower ends of the conductive base 263 respectively. In the present embodiment, the working circuit board 261 is an infrared light panel, the conductive base 263 is provided with four pairs of accommodating cavities 263', and four pairs of conductors 262 are placed in the four pairs of accommodating cavities 263' respectively. In the present embodiment, the conductors 262 are conductive steel balls, and diameters of the conductors 262 are less than or equal to diameters of the accommodating cavities 263', so that the conductors 262 can freely rotate inside the accommodating cavities 263'; both of the two first conductive parts 266 are positioned on a bottom surface of the working circuit board 261, and both of the two first conductive parts 266 are connected with the working circuit board 261; both of the two second conductive parts 267 are positioned on a top surface of the conductive plate 264, and both of the two second conductive parts 267 are connected with the conductive plate 264; and top surfaces of the four pairs of conductors 262 are connected with the two first conductive parts 266 in an abutting mode respectively, and bottom surfaces of the four pairs of conductors 262 are connected with the two second conductive parts 267 in an abutting mode respectively. In the present embodiment, the two first conductive parts 266 are positioned right above the two second conductive parts 267, the two first conductive parts 266 are concentric circles, and the two second conductive parts 267 and the two first conductive parts 266 have a same shape and size; the four pairs of accommodating cavities 263' correspond to the two first conductive parts 266 and the two second conductive parts 267 respectively; the two first conductive parts 266 are a first conductive ring 2661 and a second conductive ring 2662; the two second conductive parts 267 are a third conductive ring 2671 and a fourth conductive ring 2672; the first conductive ring 2661 and the third conductive ring 2671 are positive electrodes, and the second conductive ring 2662 and the fourth conductive ring 2672 are negative electrodes; and the first conductive ring 2661 of the working circuit board 261 and the third conductive ring 2671 of the conductive plate 264 are connected in an abutting mode through the conductors 262, and the second conductive ring 2662 of the working circuit board 261 and the fourth conductive ring 2672 of the conductive plate 264 are connected in an abutting mode through the conductors 262 to ensure that current can be transmitted to the conductors 262 through the second conductive parts 267 of the conductive plate 264, and then the current can be transmitted to the first conductive parts 266 of the working circuit board 261 through the conductors 262, so that the working circuit board 261 can be electrified to work.

Figure 1:
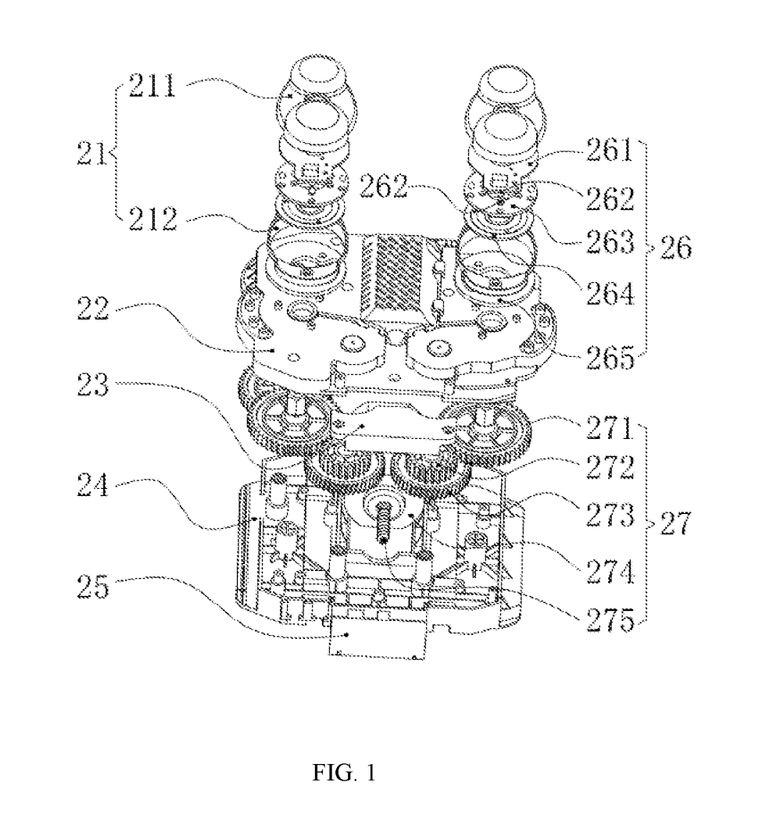
FIG. 1 is an exploded view of a massage roller of the disclosure.
Figure 2:
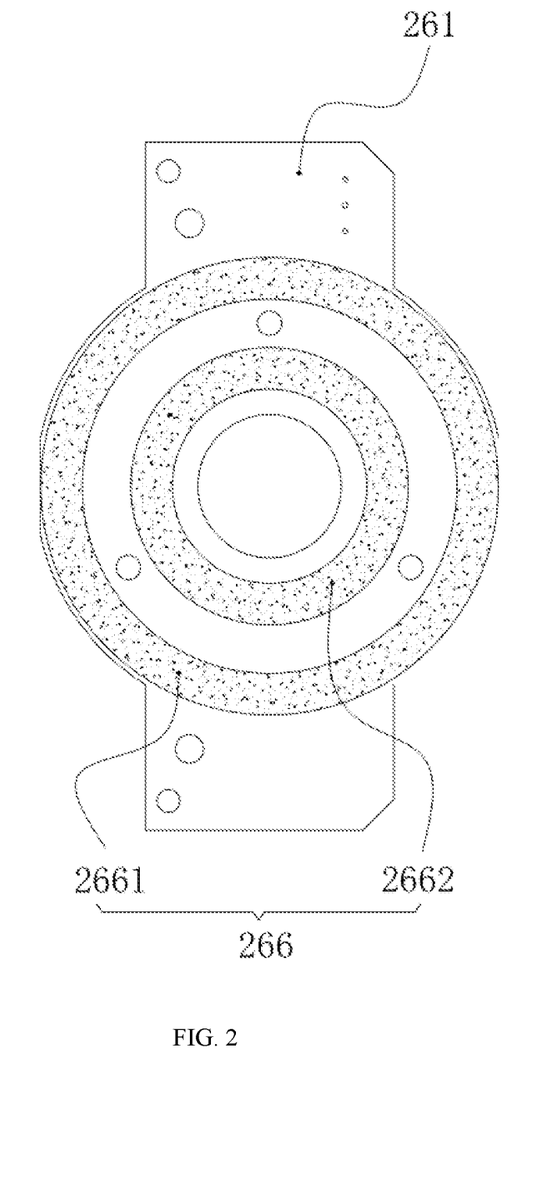
FIG. 2 is a schematic diagram of a bottom view of a working circuit board of the disclosure.
Figure 3:
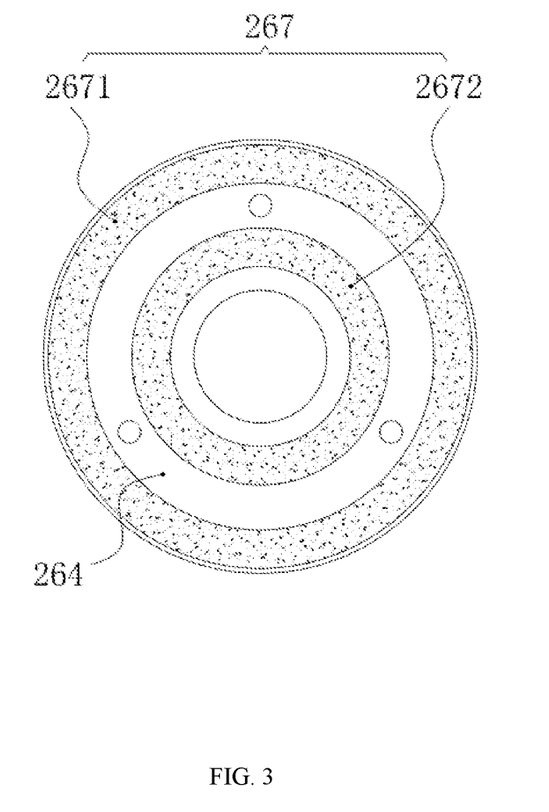
FIG. 3 is a schematic diagram of a top view of a conductive plate of the disclosure.
Figure 4:
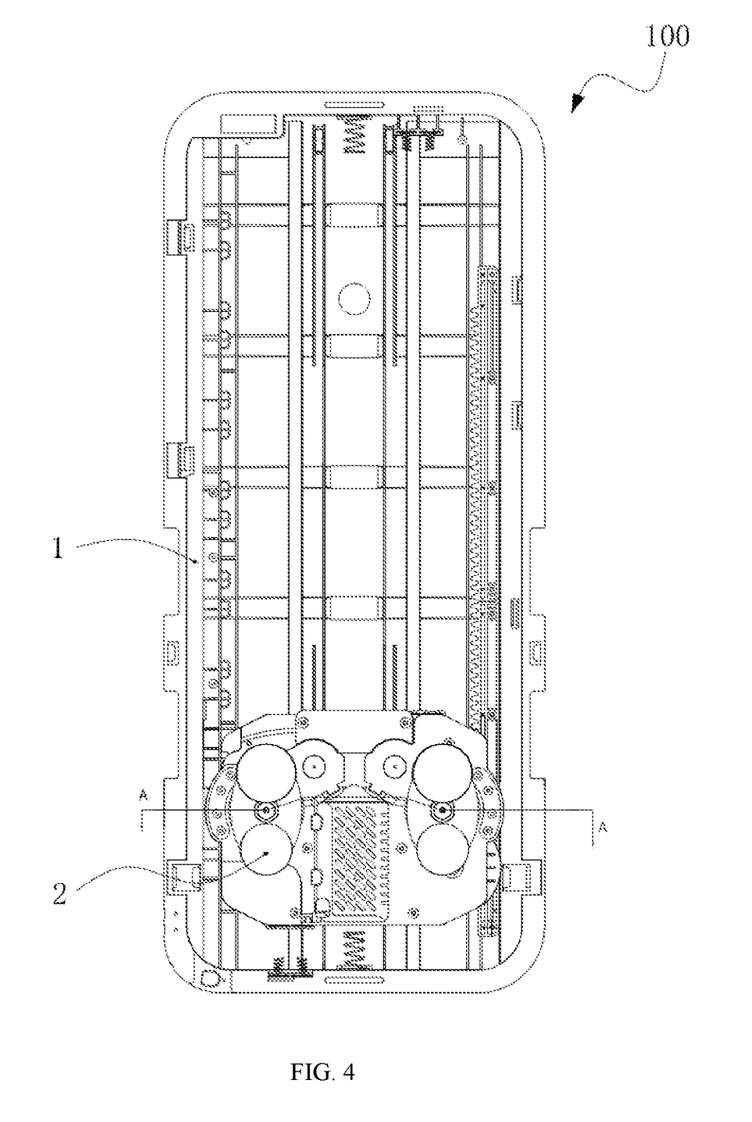
FIG. 4 is a schematic diagram of a top view after a massage roller of the disclosure and a machine body are assembled.

The number of the accommodating cavities 263' on the conductors 262 and the conductive base 263 is not limited to four pairs, and the number of the conductors 262 and the number of the accommodating cavities 263' can be increased or decreased according to actual needs, as long as the number of the accommodating cavities 263' is multiples of the number of the conductors 262.

As shown in FIG. 1 and FIGS. 4-8, a massage roller 2 includes two massage heads 21, an upper roller cover 22, a center box cover 23, a lower roller cover 24, a control circuit board 25 and a driving mechanism 27; the two massage heads 21 are rotatably connected to two ends of a top surface of the upper roller cover 22 respectively; the upper roller cover 22 is detachably and can be connected above the lower roller cover 24; the center box cover 23 is positioned on a top surface of one side of the upper roller cover 22; the control circuit board 25 is positioned at one side of the center box cover 23; the driving mechanism 27 is fixed between a locking upper roller cover 22 and the lower roller cover 24 and used for driving the two massage heads 21 to rotate; the massage roller further includes two conductive structures 26 as mentioned above; and the working circuit boards 261 of the two conductive structures 26 are fixed inside the two massage heads 21 respectively, and the two conductive bases 263 and the two conductive plates 264 are fixed on the upper roller cover 22 below the two massage heads 21.

A bottom edge of the upper roller cover 22 and a top edge of the lower roller cover 24 are respectively provided with a convex part and a concave part which can be mutually connected in a clamped mode. The upper roller cover 22 is provided with a plurality of screw holes, and the lower roller cover 24 is provided with a plurality of fixed legs corresponding to the screw holes, so that after the upper roller cover 22 and the lower roller cover 24 are clamped, the upper roller cover 22 and the lower roller cover 24 can be locked and fixed to the fixed legs by making fixing bolts penetrate through the screw holes, and the fixation, disassembly and assembly of the upper roller cover 22 and the lower roller cover are achieved. A fixing groove matched with the center box cover 23 in shape and a connecting leg connected with the center box cover 23 are further arranged at the top of the upper roller cover 22 for assembly, clamp-fixing and bolt locking between the upper roller cover 22 and the center box cover 23.

The upper roller cover 22 and the lower roller cover 24 are not only connected in the above-mentioned manner, but can also be connected by other means such as buckles, as long as the upper roller cover 22 and the lower roller cover 24 can be detachably connected.

Figure 7:
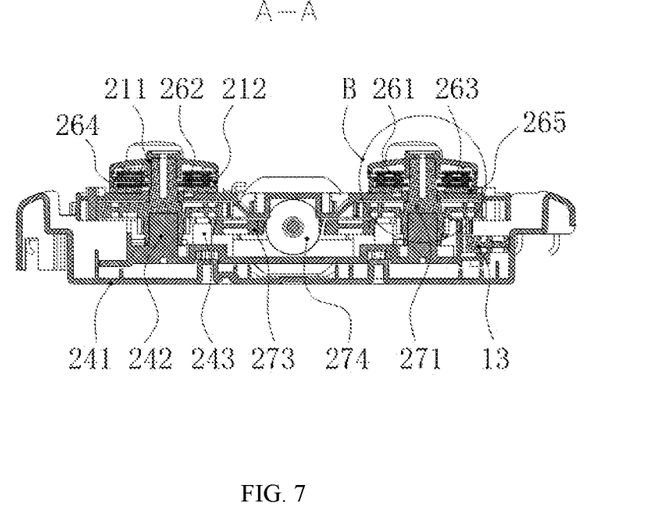
FIG. 7 is a cross-sectional schematic diagram of A-A in FIG. 4.
Figure 8:
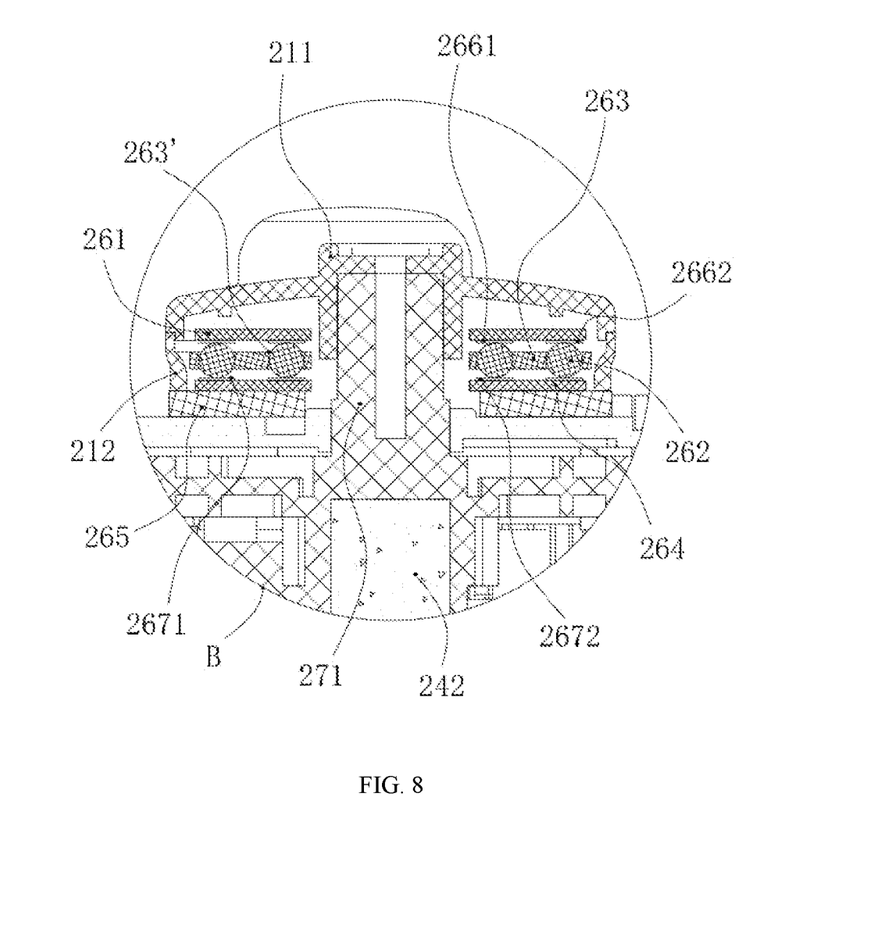
FIG. 8 is a schematic enlarged structural diagram of B in FIG. 7.

As shown in FIG. 1 and FIGS. 7-8, in the present embodiment, the massage head 21 includes an upper massage head cover 211 and a lower massage head cover 212. The upper massage head cover 211 is detachably connected above the lower massage head cover 212. A center of the lower massage head cover 212 is provided with an accommodating cavity, and the working circuit board 261 is detachably connected above the accommodating cavity of the lower massage head cover 212. The conductive base 263 and the conductive plate 264 are positioned in the accommodating cavity of the lower massage head cover 212, so that when the massage head 21 is driven by the driving mechanism 27 to rotate, the working circuit board 261 of the conductive structure 26 can rotate with the massage head 21, but the conductive base 263 and the conductive plate 264 of the conductive structure 26 do not rotate, so that the working circuit board 261 can still make contact with the conductive plate 264 through the conductors 262 during rotation, it is ensured that the working circuit board 261 can be electrified to work, and the skin tissue of the user can be irritated by the light beads on the working circuit board 261, thereby promoting the blood circulation of the user and improving the massage effect of the massage head 21.

Figure 6:
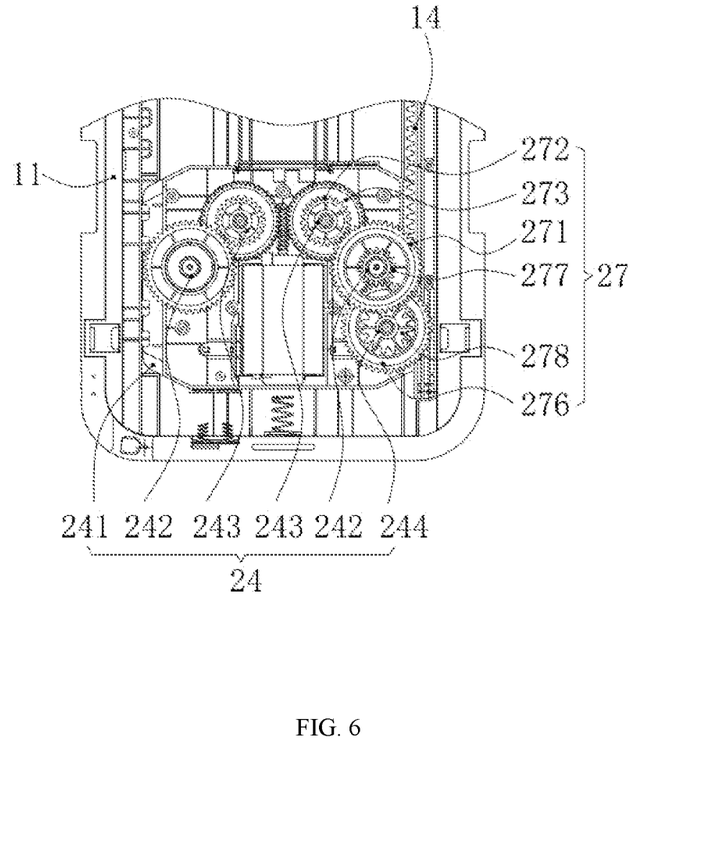
FIG. 6 is a schematic diagram of a top view of a driving mechanism after a massage roller of the disclosure and a machine body are assembled.

As shown in FIGS. 1 and 6, in the present embodiment, the lower roller cover 24 includes a housing 241, two main fixed legs 242, two auxiliary fixed legs 243, an accommodating groove and a connecting fixed leg 244. The accommodating groove is formed in the center of the interior of the housing 241. The two main fixed legs 242, the two auxiliary fixed legs 243 and the connecting fixed leg 244 are all positioned inside the housing 241 outside the accommodating groove, and the two main fixed legs 242 and the two auxiliary fixed legs 243 are symmetrical about the accommodating groove. The connecting fixed leg 244 is positioned at the same side with one of the main fixed legs 242 and one of the auxiliary fixed legs 243, the housing 241 is provided with an opening at the side provided with the connecting fixed leg 244, and the auxiliary fixed leg 243 and the connecting fixed leg 244 are positioned at two ends of the main fixed leg 242 at the corresponding side.

Figure 5:
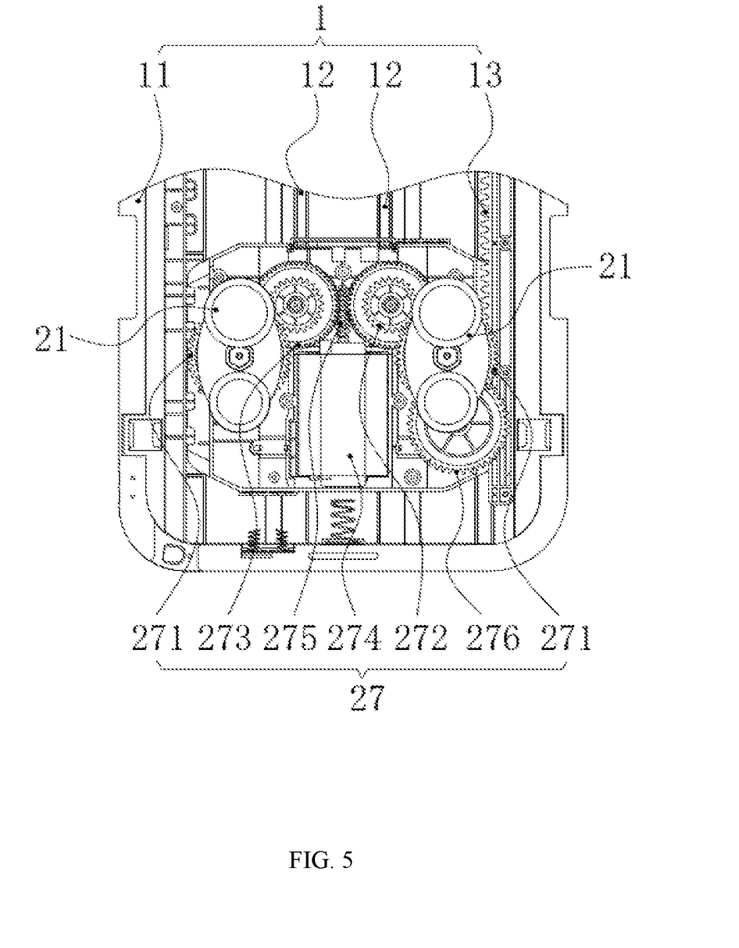
FIG. 5 is a schematic diagram of a partial top view with an upper roller cover removed after a massage roller of the disclosure and a machine body are assembled.

As shown in FIG. 1 and FIGS. 5-6, in the present embodiment, the driving mechanism 27 includes two main gears 271, two auxiliary gears 272, two driving gears 273, a motor 274, a main linkage gear 276, an auxiliary linkage gear 277 and a traveling gear 278. The two main gears 271 are installed on the two main fixed legs 242 respectively in a sleeving mode, the auxiliary linkage gear 277 is installed on the main fixed leg 242 at one end of the connecting fixed leg 244 in a sleeving mode, the main gears 271 are positioned above the auxiliary linkage gear 277, and the two main gears 271 are positioned on the same horizontal plane. The two auxiliary gears 272 and the two driving gears 273 are installed on the two auxiliary fixed legs 243 respectively in a sleeving mode, the two auxiliary gears 272 are positioned above the two driving gears 273, and the two auxiliary gears 272 mutually mesh with the two main gears 271 respectively. The motor 274 is positioned in the accommodating groove, an output end of the motor 274 is connected with a screw rod 275, and two sides of the screw rod 275 mutually mesh with the two driving gears 273 respectively. The main linkage gear 276 and the traveling gear 278 are installed on the connecting fixed leg 244 in a sleeving mode respectively, the main linkage gear 276 is positioned above the traveling gear 278, the main linkage gear 276 meshes with the auxiliary linkage gear 277 mutually, and the main linkage gear 276 and the traveling gear 278 partially penetrate through the opening and extend to the outside of the lower roller cover 24. In the present embodiment, a center of each main gear 271 is provided with a columnar protrusion, and a center of the conductive structure 26 is provided with a through hole; the columnar protrusions penetrate through the through hole of the conductive structure 26 and are connected with the massage heads 21, so that when the motor 274 is electrified to work, the two driving gears 273 are driven to rotate by the screw rod 275; at this point, the two auxiliary gears 272 rotate synchronously with the two driving gears 273, and then engage with the two main gears 271 to rotate, and the rotating main gears 271 drive the massage heads 21 to rotate so as to massage the user through the rotating massage heads 21. In actual production, the number of the massage heads 21, the number of the main gears 271, the number of the auxiliary gears 272 and the number of the driving gears 273 can be increased or decreased as needed to ensure that the massage roller 2 can meet different use requirements.

As shown in FIGS. 4-7, in the present embodiment, a massage roller 2 is installed inside a massager housing 1, and a complete massager 100 is formed by the massage roller 2 and the massager housing 1 for massage use of the user. The massager housing 1 includes a machine body 11, two guide rails 12 and a rack 13. The two guide rails 12 are positioned at an inner bottom end of the machine body 11, and the massage roller 2 is slidably connected between the two guide rails 12. The rack 13 is positioned on the inner wall of one side of the machine body 11, and the main linkage gear 276 of the massage roller 2 meshes with the rack 13 mutually, so that when the motor 274 drives the two main gears 271 and the massage heads 21 to rotate, the auxiliary linkage gear 277 rotates synchronously with the main gears 271 and engages with the main linkage gear 276 to rotate, at the same time, the traveling gear 278 rotates synchronously with the main linkage gear 276, and the massage roller 2 is driven to move along the guide rails 12 under the action of the rack 13, realizing the movement of the massage roller 2, thereby providing the user with an all-around massage through the moving massage roller 2 and the rotating massage heads 21; and preferably, there are two massage rollers 2 in each massager housing 1, but the number of the massage rollers 2 is not limited to two and can be increased according to actual use requirements.

Embodiment 2

As shown in FIGS. 7 and 8, in the present embodiment, a cushion block 265 is further arranged between a bottom of the massage head 21 and the upper roller cover 22, and the cushion block 265 is fixed on a surface of the upper roller cover 22 below the conductive plate 264 and used for improving the sealing property between the massage head 21 and the upper roller cover 22, and reducing the friction between the bottom of the massage head 21 and the upper roller cover 22, thereby prolonging the service life of the massage head 21.

Other structures are the same as those in Embodiment 1.

The installation sequence of the present embodiment of the application is as follows: firstly, the driving mechanism 27 is installed in the lower roller cover 24, and then the upper roller cover 22 is closed, so that the driving mechanism 27 is positioned between the upper roller cover 22 and the lower roller cover 24, and the columnar protrusion at the center of the main gear 271 in the driving mechanism 27 penetrates through the upper roller cover 22 and extends to the upper part of the upper roller cover 22; then, the center box cover 23 and the control circuit board 25 are assembled with the upper roller cover 22 and the lower roller cover 24, so that the control circuit board 25 is electrically connected with the motor 274 of the driving mechanism 27; then, the conductive plate 264 is installed outside the columnar protrusion at the center of the main gear 271 above the upper roller cover 22 in a sleeving mode, and the conductive base 263 is placed above the conductive plate 264, so that the conductors 262 are placed inside the accommodating cavities 263' of the conductive base 263, and the conductors 262 abut against the third conductive ring 2671 and the fourth conductive ring 2672 of the conductive plate 264; then, the working circuit board 261 is installed on the lower massage head cover 212 by screws, and the lower massage head cover 212 provided with the working circuit board 261 is placed above the conductive base 263 and the conductive plate 264, so that the first conductive ring 2661 and the second conductive ring 2662 of the working circuit board 261 and the conductors 262 are positioned directly above the third conductive ring 2671 and the fourth conductive ring 2672; then, the upper massage head cover 211 of the massage head 21 is in butt-joint with the lower massage head cover 212 of the massage head 21, the upper massage head cover 211 is fixed to the columnar protrusion at the center of the main gear 271, and the first conductive ring 2661 and the second conductive ring 2662 of the working circuit board 261 press towards the conductors 262 along with the connection between the upper massage head cover 211 and the lower massage head cover 212, so that the first conductive parts 266 of the working circuit board 261 abut against the second conductive parts 267 of the conductive plate 264 through the conductors 262 to conduct electricity; then the conductive plate 264 is electrically connected with the control circuit board 25; and finally, the assembled massage roller 2 is installed in the massager housing 1, the traveling gear 278 of the massage roller 2 and the rack 13 of the massager housing 1 mesh with each other, a bottom of the massage roller 2 is slidably connected with the two guide rails 12 of the massager housing 1, and the control circuit board 25 is electrically connected with a main control panel of the massager 100, thus completing the installation of the massager 100.

When using the massager 100, the user first turns on an external power supply to make the control circuit board 25 work under the driving of the main control panel of the massager 100, so that the conductive plate 264 and the motor 274 are electrified to work. The motor 274 drives the screw rod to rotate, and the screw rod drives the two driving gears 273 to rotate. At this point, the two auxiliary gears 272 rotate synchronously with the two driving gears 273, and then engage with the two main gears 271 to rotate, and the rotating main gears 271 drive the massage head 21 to rotate, so that the user is massaged through the rotating massage head 21. When the massage head 21 rotates, the working circuit board 261 rotates along with it, while the conductive base 263 and the conductive plate 264 are in a stationary state. The working circuit board 261 drives the first conductive parts 266 to constantly generate friction with the conductors 262, and the conductors 262 rotate relatively in the accommodating cavities 263' and abut against the first conductive parts 266 of the working circuit board 261 and the second conductive parts 267 of the conductive plate 264 all the time. In this way, the conductive plate 264 can continuously transmit current into the conductors 262 through the second conductive parts 267, and the conductors 262 can transmit the current to the first conductive parts 266 of the working circuit board 261, so that the working circuit board 261 can be electrified to work, and when serving as a light panel, the working circuit board 261 irradiates the skin tissue of the user through the light beads, thus promoting the blood circulation of the user and improving the massage effect of the massage head 21. The rotating conductors 262 can effectively avoid the local hard friction of the conductive contact surface, so that the friction loss of the conductors 262 is reduced, poor contact and open circuit of the working circuit board 261 are avoided, and the conductive effect is good. When the massage head 21 rotates under the action of the driving mechanism 27, the auxiliary linkage gear 277 of the driving mechanism 27 rotates synchronously with the main gears 271 and engages with the main linkage gear 276 to rotate, and the traveling gear 278 can rotate synchronously with the main linkage gear 276, so that the massage roller 2 moves along the guide rails 12 in the massager housing 1 under the action of the rack 13, and an all-around massage is provided for the user through the moving massage roller 2 and the rotating massage head 21.

To sum up, according to the massage roller and the conductive structure thereof provided by the disclosure, in the conductive structure 26, by arranging the conductive base 263 between the working circuit board 261 and the conductive plate 264 and allowing the conductors 262 placed in the conductive base 263 to make contact with the first conductive parts 266 and the second conductive parts 267 of the working circuit board 261 and the conductive plate 264, the working circuit board 261 abuts against the conductors 262 all the time while rotating along with the massage head 21, in this way, the working circuit board 261 is kept in an electrified state, so that the infrared light beads on the working circuit board 261 can irradiate the skin tissue of the user, thus promoting the blood circulation of the user and improving the massage effect of the massage head; and the rotating conductors 262 can effectively avoid the local hard friction of the conductive contact surface, thus reducing the friction loss of the conductors 262, avoiding poor contact and open circuit of the working circuit board 261, producing a good conductive effect, and prolonging the service life of the massager 100.

In the description of the disclosure, it should be understood that directional or positional relationships indicated by the terms such as "center", "longitudinal", "transverse", "length", "width", "thickness", "upper", "lower", "front", "rear", "left", "right", "vertical", "horizontal", "top", "bottom", "inner", "outer", "clockwise" and "counterclockwise" are based on the directional or positional relationships shown in the drawings, which are only for the convenience of describing the disclosure and simplifying the description, but do not indicate or imply that the referred devices or elements must have a specific orientation or be constructed and operated in a specific orientation, so they cannot be understood as limiting the disclosure.

In the description of this specification, descriptions referring to the terms "one embodiment", "some embodiments", "example", "specific example", or "some examples" mean that specific features, structures, materials or characteristics described in connection with the embodiment or example are included in at least one embodiment or example of the disclosure. In this specification, the schematic expression of the above terms should not be understood as necessarily referring to the same embodiment or example. Furthermore, the specific features, structures, materials or characteristics described may be combined in any one or more embodiments or examples in a suitable manner. In addition, those skilled in the art can join and combine different embodiments or examples described in this specification.

Although the embodiments of the disclosure have been shown and described above, it can be understood that the above-mentioned embodiments are exemplary and cannot be understood as limiting the disclosure, and those of ordinary skill in the art can make changes, modifications, substitutions and variations to the above-mentioned embodiments within the scope of the disclosure.

What is claimed is:

1. A massage roller, comprising:
    a massage head,
    an upper roller cover,
    a center box cover,
    a lower roller cover,
    a control circuit board, and
    a driving mechanism,
    wherein the massage head is rotatably connected to a top surface of the upper roller cover; the upper roller cover is detachably connected above the lower roller cover; the center box cover is positioned on a top surface of one side of the upper roller cover; the control circuit board is positioned at one side of the center box cover; the driving mechanism is fixed between a locking upper roller cover and the lower roller cover and used for driving the massage head to rotate; and further comprising a conductive structure comprising:
    a working circuit board,
    a conductive base,
    a conductive plate,
    two first conductive parts and two second conductive parts,
    wherein the working circuit board and the conductive plate are positioned at upper and lower ends of the conductive base respectively; the conductive base is provided with at least one pair of accommodating cavities, and conductors are placed in the at least one pair of accommodating cavities; the two first conductive parts are positioned on a bottom surface of the working circuit board, and both of the two first conductive parts are connected with the working circuit board; the two second conductive parts are positioned on a top surface of the conductive plate, and both of the two second conductive parts are connected with the conductive plate; and top surfaces of the conductors are connected with the two first conductive parts in an abutting mode respectively, and bottom surfaces of the conductors are connected with the two second conductive parts in an abutting mode respectively, and
    wherein the working circuit board of the conductive structure is fixed inside the massage head, and the conductive base and the conductive plate are fixed on the upper roller cover below the massage head.

2. The massage roller according to claim 1, wherein the massage head comprises an upper massage head cover and a lower massage head cover; the upper massage head cover is detachably connected above the lower massage head cover; a center of the lower massage head cover is provided with a cavity, and the working circuit board is detachably connected above the cavity of the lower massage head cover; and the conductive base and the conductive plate are positioned in the cavity of the lower massage head cover.

3. The massage roller according to claim 1, wherein a cushion block is arranged between a bottom of the massage head and the upper roller cover, and the conductive base and the conductive plate are placed above the cushion block.

4. The massage roller according to claim 1, wherein the lower roller cover comprises a housing, a main fixed leg, an auxiliary fixed leg, an accommodating groove and a connecting fixed leg; the accommodating groove is formed in a center of an interior of the housing, and the main fixed leg, the auxiliary fixed leg and the connecting fixed leg are positioned inside the housing outside the accommodating groove; and the auxiliary fixed leg and the connecting fixed leg are positioned at two ends of the main fixed leg respectively.

5. The massage roller according to claim 4, wherein the driving mechanism at least comprises a main gear, an auxiliary gear, a driving gear, a motor, a main linkage gear, an auxiliary linkage gear and a traveling gear; the main gear and the auxiliary linkage gear are installed on the main fixed leg in a sleeving mode respectively, and the main gear is positioned above the auxiliary linkage gear; the auxiliary gear and the driving gear are installed on the auxiliary fixed leg in a sleeving mode respectively, the auxiliary gear is positioned above the driving gear, and the auxiliary gear meshes with the main gear mutually; the motor is positioned in the accommodating groove, and an output end of the motor is connected with a screw rod, wherein the screw rod meshes with the driving gear mutually; and the main linkage gear and the traveling gear are installed on the connecting fixed leg in a sleeving mode respectively, the main linkage gear is positioned above the traveling gear, and the main linkage gear meshes with the auxiliary linkage gear mutually.

6. The massage roller according to claim 5, wherein a center of the main gear is provided with a columnar protrusion, wherein the columnar protrusion penetrates through the conductive structure and is connected with the massage head.

7. The massage roller according to claim 1, wherein the working circuit board is an infrared light panel.

8. The massage roller according to claim 7, wherein the two first conductive parts are positioned above the two second conductive parts, the two first conductive parts are concentric circles, the two second conductive parts and the two first conductive parts have a same shape and size, and the at least one pair of accommodating cavities corresponds to the two first conductive parts and the two second conductive parts.

9. The massage roller according to claim 7, wherein the conductors are conductive steel balls, and diameters of the conductors are less than or equal to diameters of the at least one pair of accommodating cavities.

* * * * *